(12) United States Patent
Fang et al.

(10) Patent No.: US 10,562,838 B2
(45) Date of Patent: Feb. 18, 2020

(54) PROCESS FOR THE ALKOXYCARBONYLATION OF OLEFINS IN A MEDIUM HAVING A LOW BRøNSTED ACID CONCENTRATION

(71) Applicant: EVONIK DEGUSSA GMBH, Essen (DE)

(72) Inventors: Xianjie Fang, Shanghai (CN); Kaiwu Dong, Bo Zhou (CN); Helfried Neumann, Rostock (DE); Ralf Jackstell, Cuxhaven Altenwalde (DE); Matthias Beller, Ostseebad Nienhagen (DE); Dirk Fridag, Haltern am See (DE); Dieter Hess, Marl (DE); Katrin Marie Dyballa, Recklinghausen (DE); Frank Geilen, Haltern am See (DE); Robert Franke, Marl (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/651,042

(22) Filed: Jul. 17, 2017

(65) Prior Publication Data

US 2018/0022686 A1    Jan. 25, 2018

(30) Foreign Application Priority Data

Jul. 19, 2016   (EP) .................................... 16180058

(51) Int. Cl.
*C07C 67/38*   (2006.01)
*B01J 27/13*   (2006.01)

(52) U.S. Cl.
CPC .............. *C07C 67/38* (2013.01); *B01J 27/13* (2013.01)

(58) Field of Classification Search
None
See application file for complete search history.

(56) References Cited

U.S. PATENT DOCUMENTS

| | | | |
|---|---|---|---|
| 5,693,851 A | 12/1997 | Sielcken et al. | |
| 6,284,925 B1 | 9/2001 | Knochel et al. | |
| 6,335,471 B1 | 1/2002 | Eastham et al. | |
| 8,969,560 B2 | 3/2015 | Eastham et al. | |
| 9,381,503 B2 | 7/2016 | Eastham et al. | |
| 2012/0330016 A1* | 12/2012 | Eastham | B01J 31/0215 546/2 |
| 2017/0022137 A1 | 1/2017 | Dong et al. | |
| 2017/0022138 A1 | 1/2017 | Dong et al. | |
| 2017/0022139 A1 | 1/2017 | Dong et al. | |
| 2017/0022234 A1 | 1/2017 | Jennerjahn et al. | |
| 2017/0022235 A1 | 1/2017 | Dong et al. | |
| 2017/0022236 A1 | 1/2017 | Dong et al. | |

FOREIGN PATENT DOCUMENTS

| | | |
|---|---|---|
| JP | H04-215851 A | 8/1992 |
| JP | H09-501691 A | 2/1997 |
| JP | 2013-516449 A | 5/2013 |
| KR | 10-2012-0127435 | 11/2012 |
| SG | 10201605921 S | 2/2017 |
| WO | 95/06027 A1 | 3/1995 |
| WO | 2011/083305 A1 | 7/2011 |

OTHER PUBLICATIONS

Dong et al. (Nature Communication 2017, 8, 14117.*
Singapore Search Report for SG 10201705858U, dated Mar. 1, 2018 (3 pages).
Wang, L. et al. Enantioselective bis-alkoxycarbonylation of styrene catalyzed by novel chiral dipyridylphosphine cationic palladium(II) complexes. Journal of Molecular Catalysis A: Chemical, vol. 196 (2003), pp. 171-178.
Khokarale et al., Zwitterion enhanced performance in palladium-phosphine catalyzed ethylene methoxycarbonylation, Catalysis Communications 44, (2014), pp. 73-75.
William Clegg et al., "Highly active and selective catalysts for the production of methyl propanoate via the methoxycarbonylation of ethane", Chem. Commun., (1999), pp. 1877-1878.
Xianjie Fang et al., Palladium-Catalyzed Alkoxycarbonylation of Conjugated Dienes under Acid-Free Conditions: Atom-Economic Synthesis of β, γ-Unsaturated Esters**, Chem. Int. Ed (2014), pp. 9030-9034.
European Search Report dated Jan. 5, 2017 for EP 16 18 0054 (1 page).
Wang, L. et al. One-Step Synthesis of Chiral Dimethyl 2-Oxo-3-phenyl-glutarate in the Asymmetric Triple-carbonylation of Styrene. Chinese Journal of Catalysis, vol. 32, 2011, pp. 1143-1148.
Jennerjahn, R. et al. Palladium-Catalyzed Isomerization and Hydroformylation of Olefins. European Journal of Chemistry, 2009, vol. 15, pp. 6383-6388.
Armarego, Wilfred L.F., et al. Purification of Laboratory Chemicals, Butterworth Heinemann (Elsevier), 6th edition, Oxford 2009 (index and chapter abstracts provided).
Harris, Robin K. et al. NMR Nomenclature, Nuclear Spin Properties and Conventions for Chemical Shifts, Pure Appl. Chem., 2001, vol. 73, pp. 1795-1818.
Harris, Robin K. et al. Further Conventions for NMR Shielding and Chemical Shifts. Pure Appl. Chem., 2008, vol. 80, pp. 59-84.

(Continued)

*Primary Examiner* — Ana Z Muresan
(74) *Attorney, Agent, or Firm* — Smith, Gambrell & Russell, LLP

(57) ABSTRACT

Process comprising the following process steps:
a) introducing an ethylenically unsaturated compound;
b) adding a ligand-metal complex comprising Pd and a bidentate phosphine ligand, or adding a bidentate phosphine ligand and a compound which comprises Pd;
c) adding an alcohol;
d) supplying CO;
e) heating the reaction mixture, the ethylenically unsaturated compound being reacted to form an ester,
where the reaction mixture is admixed with less than 0.1 mol %, based on the amount of substance of the ethylenically unsaturated compound, of Brønsted acids having an acid strength of pKa≤3,
characterized in that the phosphine ligand is substituted on at least one phosphorus atom by at least one heteroaryl radical.

12 Claims, 1 Drawing Sheet

(56) References Cited

OTHER PUBLICATIONS

Figure 1:
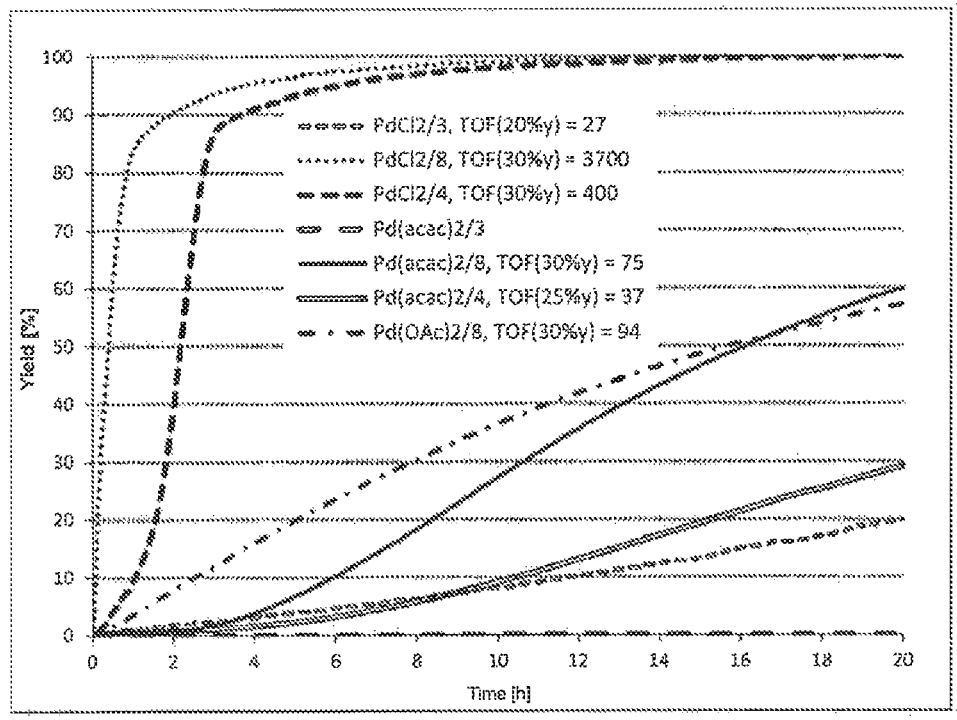

U.S. Appl. No. 15/649,743, filed Jul. 14, 2017, Dong, et al.
U.S. Appl. No. 15/649,759, filed Jul. 14, 2017, Dong, et al.
U.S. Appl. No. 15/649,770, filed Jul. 14, 2017, Dong, et al.
U.S. Appl. No. 15/649,781, filed Jul. 14, 2017, Dong, et al.
U.S. Appl. No. 15/651,169, filed Jul. 17, 2017, Dong, et al.
U.S. Appl. No. 15/651,105, filed Jul. 17, 2017, Dong, et al.
U.S. Appl. No. 15/651,062, filed Jul. 17, 2017, Dong, et al.
Köppe, Ralf, et al. Quntenchemische und Experimentelle Untersuchungen zur Stabilität und Struktur von $GaAs_5$ und $InAs_5$. Angew. Chem. 2004, vol. 116, pp. 2222-2225.
Budzelaar, Peter H.M. et al. Synthesis and Coordination Chemistry of a New Class of Binucleating Ligands: Pyridyl-Substituted Diphosphines. Organometallics, 1990, vol. 9, pp. 1222-1227.
Japanese Office Action dated Oct. 16, 2018 for JP Patent Application No. 2017137958 (4 pages in Japanese with English machine translation).
Search Report dated Mar. 12, 2019 for Taiwan Patent Application No. 106123834 (1 page in Chinese with English machine translation).
Korean Office Action dated Jan. 8, 2019 for KR Patent Application No. 10-2017-0090732 (6 pages in Korean with English machine translation).

* cited by examiner

PROCESS FOR THE ALKOXYCARBONYLATION OF OLEFINS IN A MEDIUM HAVING A LOW BRØNSTED ACID CONCENTRATION

The present invention relates to a process for the alkoxycarbonylation of olefins, wherein the alkoxycarbonylation takes place in a medium having a low Brønsted acid concentration.

The alkoxycarbonylation of alkenes is a process of increasing significance. An alkoxycarbonylation is understood to mean the reaction of unsaturated compounds such as olefins, with carbon monoxide and alcohols in the presence of a metal or of a metal complex and of a ligand to give the corresponding esters:

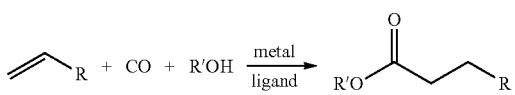

Scheme 1: General reaction equation of the alkoxycarbonylation of an ethylenically unsaturated compound.

Among the alkoxycarbonylation reactions the ethene methoxycarbonylation to give 3-methyl-propionate is of significance as an intermediate stage for the preparation of methyl methacrylate (S. G. Khokarale, E. J. Garcia-Suarez, J. Xiong, U. V. Mentzel, R. Fehrmann, A. Rilsager, Catalysis Communications 2014, 44, 73-75). Ethene methoxycarbonylation is conducted in methanol as solvent under mild conditions with a palladium catalyst modified by phosphine ligands. A very good catalytic system was developed by Lucite now Mitsubishi Rayon and uses a ligand based on 1,2-bis(di-tert-butylphosphinomethyl)benzene (DTBPMB) (W. Clegg, G. R. Eastham, M, R. J. Elsegood, R. P. Tooze, X. L. Wang, K. Whiston, Chern. Commun. 1999, 1877-1878).

The alkoxycarbonylation is customarily carried out with addition of strong Brønsted acids, examples being para-toluenesulphonic acid, methanesulphonic acid or sulphuric acid. This, however, is a disadvantage for the industrial use of the alkoxycarbonylation, since it entails increased corrosion of the reactors and other equipment.

One known acid-free process is based on the use of 4,5-bis(diphenylphosphino)-9,9-dimethylxanthene (xantphos) as a bidentate ligand (Fang, X., Li, H., Jackstell, R. and Beller, M., 2014, Palladium-Catalyzed Alkoxycarbonylation of Conjugated Dienes under Acid-Free Conditions: Atom-Economic Synthesis of β,γ-Unsaturated Esters. Angew. Chem. Int. Ed., 53: 9030-9034). For a number of further bidentate ligands, however, it has been found that they are not suitable for the acid-free alkoxycarbonylation (Fang, X. et al., loc. cit.).

The problem addressed by the present invention is therefore that of providing a process for the alkoxycarbonylation of olefins wherein the addition of Brønsted acids can be kept low and wherein good yields can be achieved.

This object is achieved by means of a process comprising the following process steps:
a) introducing an ethylenically unsaturated compound;
b) adding a ligand-metal complex comprising Pd and a bidentate phosphine ligand, or adding a bidentate phosphine ligand and a compound which comprises Pd;
c) adding an alcohol;
d) supplying CO;
e) heating the reaction mixture, the ethylenically unsaturated compound being reacted to form an ester,
where the reaction mixture is admixed with less than 0.1 mol %, based on the amount of substance of the ethylenically unsaturated compound, of Brønsted acids having an acid strength of $pK_a \leq 3$,
characterized in that the phosphine ligand is substituted on at least one phosphorus atom by at least one heteroaryl radical.

In this process, process steps a), b), c) and d) can be effected in any desired sequence. Typically, however, the addition of CO is effected after the co-reactants have been initially charged in steps a) to c). Steps d) and e) can be effected simultaneously or successively. In addition, CO can also be fed in in two or more steps, in such a way that, for example, a portion of the CO is first fed in, then the mixture is heated, and then a further portion of CO is fed in.

Through the inventive use of a bidentate phosphine ligand which is substituted on at least one phosphorus atom by at least one heteroaryl radical it is possible to carry out the alkoxycarbonylation of ethylenically unsaturated compounds without adding strong Brønsted acids having an acid strength of $pK_a \leq 3$, or with addition of not more than 0.1 mol %, based on the amount of substance of the ethylenically unsaturated compound, without any accompanying losses in yield. As a result, in particular, corrosion problems are avoided, and/or it is unnecessary to use expensive, acid-resistant steels in the large-scale plant.

The amount of added Brønsted acid having an acid strength of $pK_a \leq 3$ in the reaction mixture is preferably less than 0.01 mol %, preferably less than 0.001 mol %, very preferably less than 0.0001 mol %, most preferably 0 mol %, based on the amount of substance of the ethylenically unsaturated compound. The fraction of the Brønsted acid here is calculated on the basis of the overall amount of substance of all added Brønsted acids having an acid strength of $pK_a \leq 3$. The amount of substance of the ethylenically unsaturated compound that is used as a basis is the overall amount of substance of the ethylenically unsaturated compound introduced.

For the purposes of this invention, the term "Brønsted acids" refers to compounds which are able to give up protons (proton donors). This term therefore does not include Lewis acids (electron pair acceptors), which are unable to give up protons, such as the Pd compound $PdCl_2$, for example.

The term "acid-free" in connection with this invention therefore relates to the circumstance wherein Brønsted acids are not added actively to the reaction mixture. This is not to rule out entirely the formation of Brønsted acids as a result of the reaction course.

The reported acid strength $pK_a$ is based on the $pK_a$ determined under standard conditions (25° C., 1.01325 bar). In the case of a polyprotic acid, the acid strength $pK_a$ in the context of this invention relates to the $pK_a$ of the first protolysis step.

The process of the invention is preferably also carried out without addition of a less strong Brønsted acid of $pKa \leq 5$, preferably $pK_a \leq 6$. Preferably, therefore, the fraction of Brønsted acid having an acid strength of $pK_a \leq 5$, preferably $pK_a \leq 6$, in the reaction mixture is less than 0.1 mol %, preferably less than 0.01 mol %, more preferably still less than 0.001 mol %, very preferably less than 0.0001 mol %, most preferably 0 mol %, based on the amount of substance of the ethylenically unsaturated compound.

Bidentate phosphine ligands for the purposes of this invention are ligands which comprise two phosphine groups, where the phosphorous atoms of both phosphine groups are able together to coordinate a palladium atom. It has emerged that as a result of at least one phosphorous atom being substituted by at least one heteroaryl group, it is possible to achieve a high yield in the acid-free alkoxycarbonylation.

The heteroaryl group is preferably a —$(C_3$-$C_{20})$-heteroaryl group.

Suitable heteroaryl groups are, for example, furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

Particularly preferred are heteroaryl groups having five to ten ring atoms, preferably five or six ring atoms.

The stated heteroaryl groups may be substituted here by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_6$-$C_{20})$-aryl, —$(C_5$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, —$NH_2$, halogen.

Preferred here are substituents selected from —$(C_1$-$C_{12})$-alkyl, —$(C_3$-$C_{12})$-cycloalkyl, —O—$(C_1$-$C_{12})$-alkyl, —O—$(C_3$-$C_{12})$-cycloalkyl, —$(C_6$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl.

Particularly preferred is substitution of the phosphorous atoms of both phosphine groups by at least one heteroaryl group.

In one preferred embodiment the bidentate phosphine ligand is selected from a compound according to one of the formulae (I) and (II)

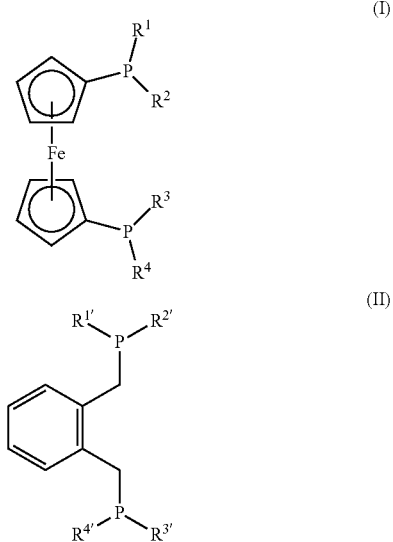

where
$R^1$, $R^2$, $R^3$, $R^4$, $R^{1'}$, $R^{2'}$, $R^{3'}$, $R^{4'}$ are each independently selected from —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl, —$(C_3$-$C_{20})$-heteroaryl; at least one of the $R^1$, $R^2$, $R^3$, $R^4$ radicals or at least one of the $R^{1'}$, $R^{2'}$, $R^{3'}$, $R^{4'}$ radicals is a —$(C_3$-$C_{20})$-heteroaryl radical;

and
$R^1$, $R^2$, $R^3$, $R^4$, $R^{1'}$, $R^{2'}$, $R^{3'}$, $R^{4'}$ if they are —$(C_1$-$C_{12})$-alkyl, —$(C_3$-$C_{12})$-cycloalkyl, —$(C_3$-$C_{12})$-heterocycloalkyl, —$(C_6$-$C_{20})$-aryl or —$(C_3$-$C_{20})$-heteroaryl, may each independently be substituted by one or more substituents selected from —$(C_1$-$C_{12})$-alkyl, —$(C_3$-$C_{12})$-cycloalkyl, —$(C_3$-$C_{12})$-heterocycloalkyl, —O—$(C_1$-$C_{12})$-alkyl, —O—$(C_1$-$C_{12})$-alkyl-$(C_6$-$C_{20})$-aryl, —O—$(C_3$-$C_{12})$-cycloalkyl, —S—$(C_1$-$C_{12})$-alkyl, —S—$(C_3$-$C_{12})$-cycloalkyl, —COO—$(C_1$-$C_{12})$-alkyl, —COO—$(C_3$-$C_{12})$-cycloalkyl, —CONH—$(C_1$-$C_{12})$-alkyl, —CONH—$(C_3$-$C_{12})$-cycloalkyl, —CO—$(C_1$-$C_{12})$-alkyl, —CO—$(C_3$-$C_{12})$-cycloalkyl, —N—[$(C_1$-$C_{12})$-alkyl]$_2$, —$(C_5$-$C_{20})$-aryl, —$(C_6$-$C_{20})$-aryl-$(C_1$-$C_{12})$-alkyl, —$(C_6$-$C_{20})$-aryl-O—$(C_1$-$C_{12})$-alkyl, —$(C_3$-$C_{20})$-heteroaryl, —$(C_3$-$C_{20})$-heteroaryl-$(C_1$-$C_{12})$-alkyl, —$(C_3$-$C_{20})$-heteroaryl-O—$(C_1$-$C_{12})$-alkyl, —COOH, —OH, —$SO_3H$, ≥$NH_2$, halogen.

The expression $(C_1$-$C_{12})$-alkyl encompasses straight-chain and branched alkyl groups having 1 to 12 carbon atoms. These are preferably $(C_1$-$C_8)$-alkyl groups, more preferably $(C_1$-$C_6)$-alkyl, most preferably $(C_1$-$C_4)$-alkyl.

Suitable $(C_1$-$C_{12})$-alkyl groups are especially methyl, ethyl, propyl, isopropyl, n-butyl, iso-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1,1,2-trimethylpropyl, 1,2,2-trimethylpropyl, 1-ethylbutyl, 1-ethyl-2-methylpropyl, n-heptyl, 2-heptyl, 3-heptyl, 2-ethylpentyl, 1-propylbutyl, n-octyl, 2-ethylhexyl, 2-propylheptyl, nonyl, decyl.

The elucidations relating to the expression $(C_1$-$C_{12})$-alkyl also apply particularly to the alkyl groups in —O—$(C_1$-$C_{12})$-alkyl, —S—$(C_1$-$C_{12})$-alkyl, —COO—$(C_1$-$C_{12})$-alkyl, —CONH—$(C_1$-$C_{12})$-alkyl, —CO—$(C_1$-$C_{12})$-alkyl and —N—[$(C_1$-$C_{12})$-alkyl]$_2$.

The expression $(C_3$-$C_{12})$-cycloalkyl encompasses mono-, bi- or tricyclic hydrocarbyl groups having 3 to 12 carbon atoms. Preferably, these groups are $(C_5$-$C_{12})$-cycloalkyl.

The $(C_3$-$C_{12})$-cycloalkyl groups have preferably 3 to 8, more preferably 5 or 6, ring atoms.

Suitable $(C_3$-$C_{12})$-cycloalkyl groups are especially cyclopropyl, cyclobutyl, cyclopentyl, cyclohexyl, cycloheptyl, cyclooctyl, cyclododecyl, cyclopentadecyl, norbornyl, adamantyl.

The elucidations relating to the expression $(C_3$-$C_{12})$-cycloalkyl also apply particularly to the cycloalkyl groups in —O—$(C_3$-$C_{12})$-cycloalkyl, —S—$(C_3$-$C_{12})$-cycloalkyl, —COO—$(C_3$-$C_{12})$-cycloalkyl, —CONH—$(C_3$-$C_{12})$-cycloalkyl, —CO—$(C_3$-$C_{12})$-cycloalkyl.

The expression $(C_3$-$C_{12})$-heterocycloalkyl encompasses nonaromatic, saturated or partly unsaturated cycloaliphatic groups having 3 to 12 carbon atoms, where one or more of the ring carbon atoms are replaced by heteroatoms. The $(C_3$-$C_{12})$-heterocycloalkyl groups have preferably 3 to 8, more preferably 5 or 6, ring atoms and are optionally substituted by aliphatic side chains. In the heterocycloalkyl groups, as opposed to the cycloalkyl groups, one or more of the ring carbon atoms are replaced by heteroatoms or heteroatom-containing groups. The heteroatoms or the heteroatom-containing groups are preferably selected from O, S, N, N(=O), C(=O), S(=O). A $(C_3-C_{12})$-heterocycloalkyl group in the context of this invention is thus also ethylene oxide.

Suitable $(C_3-C_{12})$-heterocycloalkyl groups are especially tetrahydrothiophenyl, tetrahydrofuryl, tetrahydropyranyl and dioxanyl.

The expression $(C_6-C_{20})$-aryl encompasses mono- or polycyclic aromatic hydrocarbyl radicals having 6 to 20 carbon atoms. These are preferably $(C_6-C_{14})$-aryl, more preferably $(C_6-C_{10})$-aryl.

Suitable $(C_5-C_{20})$-aryl groups are especially phenyl, naphthyl, indenyl, fluorenyl, anthracenyl, phenanthrenyl, naphthacenyl, chrysenyl, pyrenyl, coronenyl. Preferred $(C_6-C_{20})$-aryl groups are phenyl, naphthyl and anthracenyl.

The expression $(C_3-C_{20})$-heteroaryl encompasses mono- or polycyclic aromatic hydrocarbyl radicals having 3 to 20 carbon atoms, where one or more of the carbon atoms are replaced by heteroatoms. Preferred heteroatoms are N, O and S. The $(C_3-C_{20})$-heteroaryl groups have 3 to 20, preferably 6 to 14 and more preferably 6 to 10 ring atoms. Thus, for example, pyridyl in the context of this invention is a $C_6$-heteroaryl radical; furyl is a $C_5$-heteroaryl radical.

Suitable $(C_3-C_{20})$-heteroaryl groups are especially furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl.

The expression halogen especially encompasses fluorine, chlorine, bromine and iodine. Particular preference is given to fluorine and chlorine.

In one embodiment, the $R^1$, $R^2$, $R^3$, $R^{1'}$, $R^{2'}$, $R^{3'}$, $R^{4'}$ radicals, if they are —$(C_1-C_{12})$-alkyl, —$(C_3-C_{12})$-cycloalkyl, —$(C_3-C_{12})$-heterocycloalkyl, —$(C_5-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —$(C_3-C_{12})$-heterocycloalkyl, —O—$(C_1-C_{12})$-alkyl, —O—$(C_1-C_{12})$-alkyl-$(C_6-C_{20})$-aryl, —O—$(C_3-C_{12})$-cycloalkyl, —S—$(C_1-C_{12})$-alkyl, —S—$(C_3-C_{12})$-cycloalkyl, —$(C_6-C_{20})$-aryl, —$(C_6-C_{20})$-aryl-$(C_1-C_{12})$-alkyl, —$(C_5-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl, —COOH, —OH, —SO$_3$H, —NH$_2$, halogen.

In one embodiment, the $R^1$, $R^2$, $R^3$, $R^4$, $R^{1'}$, $R^{2'}$, $R^{3'}$, $R^{4'}$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —$(C_3-C_{12})$-cycloalkyl, —O—$(C_1-C_{12})$-alkyl, —O—$(C_1-C_{12})$-alkyl-$(C_6-C_{26})$-aryl, —O—$(C_3-C_{12})$-cycloalkyl, —$(C_6-C_{20})$-aryl, —$(C_6-C_{20})$-aryl-$(C_1-C_{12})$-alkyl, —$(C_3-C_{20})$-aryl-O—$(C_1-C_{12})$-alkyl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$, $R^{1'}$, $R^{2'}$, $R^{3'}$, $R^{4'}$ radicals, if they are —$(C_1-C_{12})$-alkyl, —$(C_3-C_{12})$-cycloalkyl, $(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl, —O—$(C_1-C_{12})$-alkyl-$(C_6-C_{20})$-aryl, —$(C_3-C_{20})$-heteroaryl, —$(C_3-C_{20})$-heteroaryl-$(C_1-C_{12})$-alkyl, —$(C_3-C_{20})$-heteroaryl-O—$(C_1-C_{12})$-alkyl.

In one embodiment, the $R^1$, $R^2$, $R^3$, $R^4$, $R^{1'}$, $R^{2'}$, $R^{3'}$, $R^{4'}$ radicals, if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl, may each independently be substituted by one or more substituents selected from —$(C_1-C_{12})$-alkyl and —$(C_3-C_{20})$-heteroaryl.

In one embodiment, the $R^1$, $R^2$, $R^3$, $R^4$, $R^{1'}$, $R^{2'}$, $R^{3'}$, $R^{4'}$ radicals are unsubstituted if they are —$(C_1-C_{12})$-alkyl, —$(C_3-C_{12})$-cycloalkyl, or —$(C_3-C_{12})$-heterocycloalkyl, and may be substituted as described if they are —$(C_3-C_{20})$-aryl, or —$(C_3-C_{20})$-heteroaryl.

In one embodiment, the $R^1$, $R^2$, $R^3$, $R^4$, $R^{1'}$, $R^{2'}$, $R^{3'}$, $R^{4'}$ radicals are unsubstituted if they are —$(C_1-C_{12})$-alkyl, —$(C_3-C_{12})$-cycloalkyl, —$(C_3-C_{12})$-heterocycloalkyl, —$(C_6-C_{20})$-aryl, or —$(C_3-C_{20})$-heteroaryl.

In one embodiment $R^1$, $R^2$, $R^3$, $R^4$, $R^{1'}$, $R^{2'}$, $R^{3'}$ and $R^{4'}$ are each independently selected from —$(C_1-C_{12})$-alkyl, —$(C_3-C_{12})$-cycloalkyl. —$(C_3-C_{12})$-heterocycloalkyl, —$(C_6-C_{20})$-aryl, —$(C_3-C_{20})$-heteroaryl;
where
at least one of the radicals $R^1$, $R^2$, $R^3$ and $R^4$, and/or at least one of the radicals $R^{1'}$, $R^{2'}$, $R^{3'}$ and $R^{4'}$, is a —$(C_3-C_{20})$-heteroaryl radical;
and
$R^1$, $R^2$, $R^3$, $R^4$, $R^{1'}$, $R^{2'}$, $R^{3'}$ and $R^{4'}$, if they are —$(C_1-C_{12})$-alkyl, —$(C_3-C_{12})$-cycloalkyl, —$(C_3-C_{12})$-heterocycloalkyl, —$(C_6-C_{20})$-aryl or —$(C_3-C_{20})$-heteroaryl,
may each independently be substituted by one or more of the substituents described above.

In one embodiment, $R^1$, $R^2$, $R^3$, $R^4$, $R^{1'}$, $R^{2'}$, $R^{3'}$, $R^{4'}$ are each independently selected from —$(C_1-C_{12})$-alkyl, —$(C_6-C_{20})$-aryl, —$(C_3-C_{20})$-heteroaryl;
where
at least one of the $R^1$, $R^2$, $R^3$, $R^4$ radicals or at least one of the $R^{1'}$, $R^{2'}$, $R^{3'}$, $R^{4'}$ radicals is a —$(C_3-C_{20})$-heteroaryl radical;
and
$R^1$, $R^2$, $R^3$, $R^4$, $R^{1'}$, $R^{2'}$, $R^{3'}$, $R^{4'}$, if they are —$(C_1-C_{12})$-alkyl, —$(C_5-C_{20})$-aryl or $(C_3-C_{20})$-heteroaryl,
may each independently be substituted by one or more of the above-described substituents.

In one embodiment, at least two of the $R^1$, $R^2$, $R^3$, $R^4$ radicals or at least two of the $R^{1'}$, $R^{2'}$, $R^{3'}$, $R^{4'}$ radicals are a —$(C_3-C_{20})$-heteroaryl radical.

In one embodiment, the $R^1$ and $R^3$ radicals or the $R^{1'}$ and $R^{3'}$ radicals are each a —$(C_3-C_{20})$-heteroaryl radical and may each independently be substituted by one or more of the substituents described above. Preferably, the $R^2$ and $R^4$ radicals or the $R^{2'}$ and $R^{4'}$ radicals are not a —$(C_3-C_{20})$-heteroaryl radical. Particularly preferably, the $R^2$ and $R^4$ radicals or the $R^{2'}$ and $R^{4'}$ radicals are selected from —$(C_1-C_{12})$-alkyl, —$(C_3-C_{12})$-cycloalkyl, —$(C_3-C_{12})$-heterocycloalkyl, —$(C_6-C_{20})$-aryl, most preferably from —$(C_1-C_{12})$-alkyl, —$(C_3-C_{12})$-cycloalkyl, —$(C_6-C_{20})$-aryl.

In one embodiment the radicals $R^1$, $R^2$ and $R^3$ and/or the radicals $R^{1'}$, $R^{2'}$ and $R^{3'}$ are each a —$(C_3-C_{26})$-heteroaryl radical and may each independently be substituted by one or more of the above-described substituents. Preferably $R^4$ or $R^{4'}$ in this case is not a —$(C_3-C_{20})$-heteroaryl radical. More preferably $R^4$ or $R^{4'}$ in this case is selected from —$(C_1-C_{12})$-alkyl, —$(C_3-C_{12})$-cycloalkyl, —$(C_3-C_{12})$-heterocycloalkyl, —$(C_6-C_{20})$-aryl, most preferably from —$(C_1-C_{12})$-alkyl, —$(C_3-C_{12})$-cycloalkyl, —$(C_6-C_{20})$-aryl.

In one embodiment, the $R^1$, $R^2$, $R^3$ and $R^4$ or $R^{1'}$, $R^{2'}$, $R^{3'}$ and $R^{4'}$ radicals are a —$(C_6-C_{20})$-heteroaryl radical and may each independently be substituted by one or more of the substituents described above.

In one embodiment, the $R^1$, $R^2$, $R^3$ and $R^4$ or $R^{1'}$, $R^{2'}$, $R^{3'}$, and $R^{4'}$ radicals, if they are a heteroaryl radical, are each independently selected from heteroaryl radicals having five to ten ring atoms, preferably a heteroaryl radical having five or six ring atoms.

In one embodiment, the $R^1$, $R^2$, $R^3$ and $R^4$ or $R^{1'}$, $R^{2'}$, $R^{3'}$ and $R^{4'}$ radicals, if they are a heteroaryl radical, are a heteroaryl radical having six ring atoms.

In one embodiment, the $R^1$, $R^2$, $R^3$ and $R^4$ or $R^{1'}$, $R^{2'}$, $R^{3'}$ and $R^{4'}$ radicals, if they are a heteroaryl radical, are a heteroaryl radical having five ring atoms.

Preferably, the $R^1$, $R^2$, $R^3$ and $R^4$ or $R^{1'}$, $R^{2'}$, $R^{3'}$ and $R^{4'}$ radicals, if they are a heteroaryl radical, are each independently selected from furyl, thienyl, pyrrolyl, oxazolyl, isoxazolyl, thiazolyl, isothiazolyl, imidazolyl, pyrazolyl, furazanyl, tetrazolyl, pyridyl, pyridazinyl, pyrimidyl, pyrazinyl, benzofuranyl, indolyl, isoindolyl, benzimidazolyl, quinolyl, isoquinolyl, where the heteroaryl radicals mentioned may be substituted as described above.

In one embodiment, the $R^1$, $R^2$, $R^3$ and $R^4$ or $R^{1'}$, $R^{2'}$, $R^{3'}$ and $R^{4'}$ radicals, if they are a heteroaryl radical, are each independently selected from furyl, thienyl, pyrrolyl, imidazolyl, pyridyl, pyrimidyl, indolyl, where the heteroaryl radicals mentioned may be substituted as described above.

Preferably, the $R^1$, $R^2$, $R^3$ and $R^4$ or $R^{1'}$, $R^{2'}$, $R^{3'}$ and $R^{4'}$ radicals, if they are a heteroaryl radical, are each independently selected from 2-furyl, 2-thienyl, 2-pyrrolyl, 2-imidazolyl, 2-pyridyl, 2-pyrimidyl, 2-indolyl, where the heteroaryl radicals mentioned may be substituted as described above.

More preferably, the $R^1$, $R^2$, $R^3$ and $R^4$ or $R^{1'}$, $R^{2'}$, $R^{3'}$ and $R^{4'}$ radicals, if they are a heteroaryl radical, are each independently selected from 2-furyl, 2-thienyl, N-methyl-2-pyrrolyl, N-phenyl-2-pyrrolyl, N-(2-methoxyphenyl)-2-pyrrolyl, 2-pyrrolyl, N-methyl-2-imidazolyl, 2-imidazolyl, 2-pyridyl, 2-pyrimidyl, N-phenyl-2-indolyl, 2-indolyl, where the heteroaryl radicals mentioned have no further substitution.

In one embodiment, the radicals $R^1$ and $R^3$ and/or $R^{1'}$ and $R^{3'}$ are each a $—(C_3-C_{20})$-heteroaryl radical having five or six ring atoms,
where the radicals $R^2$ and $R^4$ and/or $R^{2'}$ and $R^{4'}$ are each independently selected from $—(C_1-C_{12})$-alkyl, $—(C_3-C_{12})$-cycloalkyl, $—(C_3-C_{12})$-heterocycloalkyl, $—(C_6-C_{20})$-aryl;
and
$R^1$, $R^3$, $R^{1'}$ and $R^{3'}$ and also $R^2$, $R^{2'}$, $R^4$ and $R^{4'}$, if they are $—(C_1-C_{12})$-alkyl, $—(C_3-C_{12})$-cycloalkyl, $—(C_3-C_{12})$-heterocycloalkyl or $—(C_6-C_{20})$-aryl,
may each independently be substituted by one or more of the substituents described above.

In one embodiment the radicals $R^1$ and $R^3$ and/or $R^{1'}$ and $R^{3'}$ are each a $—(C_3-C_{20})$-heteroaryl radical having five or six ring atoms, and the radicals $R^2$ and $R^4$ and/or $R^{2'}$ and $R^{4'}$ are each $—(C_1-C_{12})$-alkyl;
where
$R^1$, $R^3$, and $R^{3'}$ and also $R^2$, $R^{2'}$, $R^4$ and $R^{4'}$ may each independently be substituted by one or more of the substituents described above.

In one embodiment the radicals $R^1$ and $R^3$ and/or $R^{1'}$ and $R^{3'}$ are each a $—(C_3-C_{20})$-heteroaryl radical selected from furyl, thienyl, pyrrolyl, imidazolyl, pyridyl, pyrimidyl, indolyl,
where the radicals $R^2$ and $R^4$ are each independently selected from $—(C_1-C_{12})$-alkyl, $—(C_3-C_{12})$-cycloalkyl, $—(C_3-C_{12})$-heterocycloalkyl, $—(C_5-C_{20})$-aryl;
and
$R^1$ and $R^3$ and also $R^2$ and $R^4$, if they are $—(C_1-C_{12})$-alkyl, $—(C_3-C_{12})$-cycloalkyl, $—(C_3-C_{12})$-heterocycloalkyl or $—(C_6-C_{20})$-aryl,
may each independently be substituted by one or more of the substituents described above.

In one preferred embodiment, the bidentate phosphine ligand is a compound of formula I, where $R^1$, $R^2$, $R^3$ and $R^4$ are defined as stated above.

The bidentate phosphine ligand is preferably a compound of formula I,
where the radicals $R^1$ and $R^3$ are each a $—(C_3-C_{20})$-heteroaryl radical having five or six ring atoms;
the radicals $R^2$ and $R^4$ are each independently selected from $—(C_1-C_{12})$-alkyl, $—(C_3-C_{12})$-cycloalkyl, $—(C_3-C_{12})$-heterocycloalkyl, $—(C_6-C_{20})$-aryl;
and
$R^1$, $R^2$, $R^3$ and $R^4$ may each independently be substituted by one or more of the substituents described above.

With particular preference, the bidentate phosphine ligand is a compound of formula I, where the radicals $R^1$ and $R^3$ are each a $—(C_3-C_{20})$-heteroaryl radical having six ring atoms; the radicals $R^2$ and $R^4$ are each $—(C_1-C_{12})$-alkyl.

The following compounds of one of the formulae (8) and (4) are particularly suitable phosphine ligands for the process according to the invention:

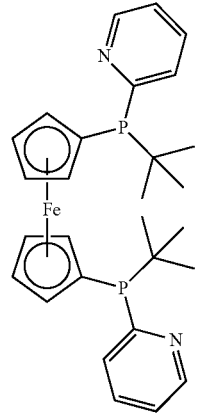

(8)

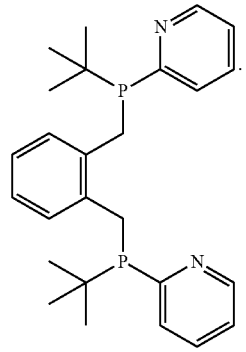

(4)

Compound 8 is particularly preferred in this context.

The ethylenically unsaturated compounds used as reactant in the process according to the invention contain one or more carbon-carbon double bonds. These compounds are also referred to hereinafter as olefins for simplification. The double bonds may be terminal or internal.

Preference is given to ethylenically unsaturated compounds having 2 to 30 carbon atoms, preferably 2 to 22 carbon atoms, more preferably 2 to 12 carbon atoms.

The ethylenically unsaturated compounds may, in addition to the one or more double bonds, contain further functional groups. Preferably, the ethylenically unsaturated compound comprises one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, hydroxyl, sulphhydryl, amino, ether, thioether, aryl, heteroaryl or silyl groups and/or halogen substituents. At the same time, the ethylenically unsaturated compound preferably comprises a total of 2 to 30 carbon atoms, preferably 2 to 22 carbon atoms, more preferably 2 to 12 carbon atoms.

In one embodiment, the ethylenically unsaturated compound does not comprise any further functional groups apart from carbon-carbon double bonds.

Suitable ethylenically unsaturated compounds are, for example:
ethene;
propene;
C4 olefins such as 1-butene, cis-2-butene, trans-2-butene, mixture of cis- and trans-2-butane, isobutene, 1,3-butadiene; raffinate I to III, crack-C4
C5 olefins such as 1-pentene, 2-pentene, 2-methyl-1-butene, 2-methyl-2-butene, 2-methyl-1,3-butadiene (isoprene), 1,3-pentadiene;
C6 olefins such as tetramethylethylene, 1,3-hexadiene, 1,3-cyclohexadiene;
C7 olefins such as 1-methylcyclohexene, 2,4-heptadiene, norbornadiene;
C8 olefins such as 1-octene, 2-octene, cyclooctene, di-n-butene, diisobutene, 1,5-cyclooctadiene, 1,7-octadiene;
C9 olefins such as tripropene;
C10 olefins such as dicyclopentadiene;
undecenes;
dodecenes;
internal C14 olefins;
internal C15 to C18 olefins;
linear or branched, cyclic, acyclic or partly cyclic, internal C15 to C30 olefins;
triisobutene, tri-n-butene;
terpenes such as limonene, geraniol, farnesol, pinene, myrcene, carvone, 3-carene;
polyunsaturated compounds having 18 carbon atoms, such as linoleic acid or linolenic acid;
esters of unsaturated carboxylic acids, such as vinyl esters of acetic or propionic acid, alkyl esters of unsaturated carboxylic acids, methyl or ethyl esters of acrylic acid and methacrylic acid, oleic esters, such as methyl or ethyl oleate, esters of linoleic or linolenic acid;
vinyl compounds such as vinyl acetate, vinylcyclohexene, styrene, alpha-methylstyrene, 2-isopropenylnaphthalene; 2-methyl-2-pentenal, methyl 3-pentenoate, methacrylic anhydride.

In one variant of the process, the ethylenically unsaturated compound is selected from propene, 1-butene, cis- and/or trans-2-butene, or mixtures thereof.

In one variant of the process, the ethylenically unsaturated compound is selected from 1-pentene, cis- and/or trans-2-pentene, 2-methyl-1-butene, 2-methyl-2-butene, 3-methyl-1-butane, or mixtures thereof.

In a preferred embodiment, the ethylenically unsaturated compound is selected from ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, n-octene, 1-octene, 2-octene, or mixtures thereof.

In one variant, a mixture of ethylenically unsaturated compounds is used. A mixture in the context of this invention refers to a composition comprising at least two different ethylenically unsaturated compounds, where the proportion of each individual ethylenically unsaturated compound is preferably at least 5% by weight, based on the total weight of the mixture.

Preference is given to using a mixture of ethylenically unsaturated compounds each having 2 to 30 carbon atoms, preferably 4 to 22 carbon atoms, more preferably 6 to 12 carbon atoms, most preferably 8 to 10 carbon atoms.

Suitable mixtures of ethylenically unsaturated compounds are those called raffinates I to III. Raffinate I comprises 40% to 50% isobutene, 20% to 30% 1-butene, 10% to 20% cis- and trans-2-butene, up to 1% 1,3-butadiene and 10% to 20% n-butane and isobutane. Raffinate II is a portion of the $C_4$ fraction which arises in naphtha cracking and consists essentially of the isomeric n-butenes, isobutane and n-butane after removal of isobutene from raffinate I. Raffinate III is a portion of the $C_4$ fraction which arises in naphtha cracking and consists essentially of the isomeric n-butenes and n-butane.

A further suitable mixture is di-n-butene, also referred to as dibutene, DNB or DnB. Di-n-butene is an isomer mixture of C8 olefins which arises from the dimerization of mixtures of 1-butene, cis-2-butene and trans-2-butene. In industry, raffinate II or raffinate III streams are generally subjected to a catalytic oligomerization, wherein the butanes present (n/iso) emerge unchanged and the olefins present are converted fully or partly. As well as dimeric di-n-butene, higher oligomers (tributene C12, tetrabutene C16) generally also form, which are removed by distillation after the reaction. These can likewise be used as reactants.

In a preferred variant, a mixture comprising isobutene, 1-butene, cis- and trans-2-butene is used. Preferably, the mixture comprises 1-butene, cis- and trans-2-butene.

The alkoxycarbonylation according to the invention is catalysed by the Pd complex. The Pd complex may either be added in process step b) as a preformed complex comprising Pd and the phosphine ligands described above or be formed in situ from a compound comprising Pd and the free phosphine ligand. In this context, the compound comprising Pd is also referred to as catalyst precursor.

In the case that the catalyst is formed in situ, the ligand can be added in excess, such that the unbound ligand is also present in the reaction mixture.

In one variant, the compound comprising Pd is selected from palladium chloride ($PdCl_2$), palladium(II) acetylacetonate [$Pd(acac)_2$], palladium(II) acetate [$Pd(OAc)_2$], dichloro (1,5-cyclooctadiene)palladium(II) [$Pd(cod)_2Cl_2$], bis(dibenzylideneacetone)palladium [$Pd(dba)_2$], bis(acetonitrile) dichloropalladium(II) [$Pd(CH_3CN)_2Cl_2$], palladium (cinnamyl) dichloride [$Pd(cinnamyl)Cl_2$].

Preferably, the compound comprising Pd is $PdCl_2$, $Pd(acac)_2$ or $Pd(OAc)_2$. $PdCl_2$ is particularly suitable.

The alcohol in process step c) may be branched or linear, cyclic, alicyclic, partly cyclic or aliphatic, and is especially a $C_1$- to $C_{30}$-alkanol. It is possible to use monoalcohols or polyalcohols.

The alcohol in process step c) comprises preferably 1 to 30 carbon atoms, more preferably 1 to 22 carbon atoms, especially preferably 1 to 12 carbon atoms. It may be a monoalcohol or a polyalcohol.

The alcohol may, in addition to the one or more hydroxyl groups, contain further functional groups. Preferably, the alcohol may additionally comprise one or more functional groups selected from carboxyl, thiocarboxyl, sulpho, sulphinyl, carboxylic anhydride, imide, carboxylic ester, sulphonic ester, carbamoyl, sulphamoyl, cyano, carbonyl, carbonothioyl, sulphhydryl, amino, ether, thioether, aryl, heteroaryl or silyl groups and/or halogen substituents.

In one embodiment, the alcohol does not comprise any further functional groups except for hydroxyl groups.

The alcohol may contain unsaturated and aromatic groups. However, it is preferably an aliphatic alcohol.

An aliphatic alcohol in the context of this invention refers to an alcohol which does not comprise any aromatic groups, i.e., for example, an alkanol, alkenol or alkynol.

In one variant of the process, the alcohol in process step c) is selected from the group of the monoalcohols.

In one variant of the process, the alcohol in process step c) is selected from: methanol, ethanol, 1-propanol, isopropanol, isobutanol, tert-butanol, 1-butanol, 2-butanol, 1-pentanol, 2-pentanol, 3-pentanol, 1-hexanol, cyclohexanol, phenol, 2-ethylhexanol, isononanol, 2-propylheptanol.

In a preferred variant, the alcohol in process step c) is selected from methanol, ethanol, 1-propanol, 1-butanol, 1-pentanol, 1-hexanol, 2-propanol, tert-butanol, 3-pentanol, cyclohexanol, phenol, and mixtures thereof.

In one variant of the process, the alcohol in process step c) is selected from the group of the polyalcohols.

In one variant of the process, the alcohol in process step c) is selected from: diols, trials, tetraols.

In one variant of the process, the alcohol in process step c) is selected from: cyclohexane-1,2-diol, ethane-1,2-diol, propane-1,3-diol, glycerol, butane-1,2,4-triol, 2-hydroxymethylpropane-1,3-diol, 1,2,6-trihydroxyhexane, pentaerythritol, 1,1,1-tri(hydroxymethyl)ethane, catechol, resorcinol and hydroxyhydroquinone.

In one variant of the process, the alcohol in process step c) is selected from: sucrose, fructose, mannose, sorbose, galactose and glucose.

In a preferred embodiment of the process, the alcohol in process step c) is selected from methanol, ethanol, 1-propanol, 1-butanol, 1-pentanol, 1-hexanol.

In a particularly preferred variant of the process, the alcohol in process step c) is selected from: methanol, ethanol.

In a particularly preferred variant of the process, the alcohol in process step c) is methanol.

In one variant of the process, the alcohol in process step c) is used in excess.

In one variant of the process, the alcohol in process step c) is used simultaneously as solvent.

In one variant of the process, a further solvent is used, selected from: toluene, xylene, tetrahydrofuran (THF) and methylene chloride ($CH_2Cl_2$).

CO is fed in in step d) preferably at a partial CO pressure between 0.1 and 10 MPa (1 to 100 bar), preferably between 1 and 8 MPa (10 to 80 bar), more preferably between 2 and 4 MPa (20 to 40 bar).

The reaction mixture is heated in step e) of the process according to the invention preferably to a temperature between 10° C. and 180° C., preferably between 20 and 160° C., more preferably between 40 and 120° C. in order to convert the ethylenically unsaturated compound to an ester.

The molar ratio of the ethylenically unsaturated compound initially charged in step a) to the alcohol added in step c) is preferably between 1:1 and 1:20, more preferably 1:2 to 1:10, more preferably 1:3 to 1:4.

The mass ratio of Pd to the ethylenically unsaturated compound initially charged in step a) is preferably between 0.001% and 0.5% by weight, preferably between 0.01% and 0.1% by weight, more preferably between 0.01% and 0.05% by weight.

The molar ratio of the bidentate phosphine ligand to Pd is preferably between 0.1:1 and 400:1, preferably between 0.5:1 and 400:1, more preferably between 1:1 and 100:1, most preferably between 2:1 and 50:1.

DESCRIPTION OF ILLUSTRATIONS

FIG. 1: effect of the palladium precursor on the methoxycarbonylation of ethylene with ligands 3, 4 and 8.

Figure 2:
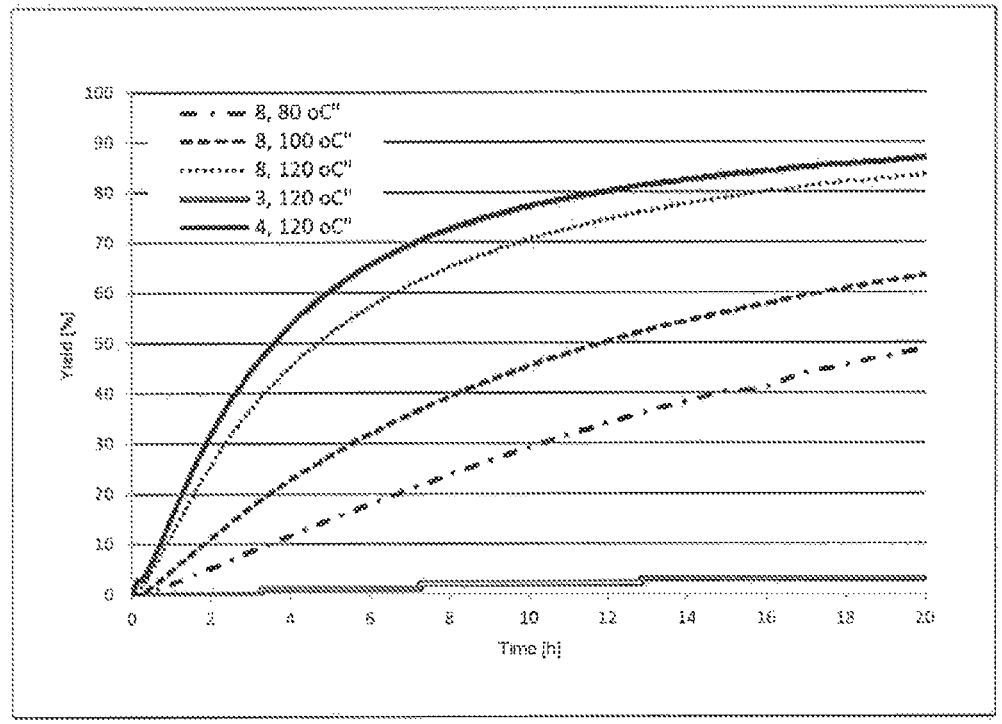

FIG. 2: acid-free methoxycarbonylation of ethene with ligands 3, 4 and 8

EXAMPLES

The invention is described in more detail below by means of working examples
General Procedures All the preparations which follow were carried out under protective gas using standard Schlenk techniques. The solvents were dried over suitable desiccants before use (Purification of Laboratory Chemicals, W. L. F. Armarego (Author), Christina Chai (Author), Butterworth Heinemann (Elsevier), 6th edition, Oxford 2009).

Phosphorus trichloride (Aldrich) was distilled under argon before use. All preparative operations were effected in baked-out vessels. The products were characterized by means of NMR spectroscopy. Chemical shifts (6) are reported in ppm. The $^{31}P$ NMR signals were referenced as follows: $SR_{31P}=SR_{1H}*(BF_{31P}/BF_{1H})=SR_{1H}*0.4048$. (Robin K. Harris, Edwin D. Becker, Sonia M. Cabral de Menezes, Robin Goodfellow, and Pierre Granger, Pure Appl. Chem., 2001, 73, 1795-1818; Robin K. Harris, Edwin D. Becker, Sonia M. Cabral de Menezes, Pierre Granger, Roy E. Hoffman and Kurt W. Zilm, Pure Appl, Chem., 2008, 80, 59-84).

The recording of nuclear resonance spectra was effected on Bruker Avance 300 or Bruker Avance 400, gas chromatography analysis on Agilent GC 7890A, elemental analysis on Leco TruSpec CHNS and Varian ICP-OES 715, and ESI-TOF mass spectrometry on Thermo Electron Finnigan MAT 95-XP and Agilent 6890 N/5973 instruments.
Preparation of Precursor E Preparation of chloro-2-pyridyl-tert-butylphosphine The Grignard for the synthesis of chloro-2-pyridyl-t-butylphosphine is prepared by the "Knochel method" with isopropylmagnesium chloride (Angew. Chem, 2004, 43, 2222-2226). The workup is effected according to the method of Budzelaar (Organometallics 1990, 9, 1222-1227).

Scheme 2: Synthesis of precursor E

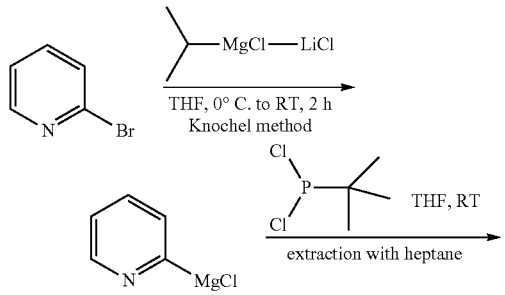

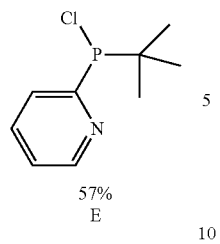

57%
E 8.07 ml of a 1.3 M isopropylmagnesium chloride solution (Knochers reagent) are introduced into a 50 ml round-bottom flask with magnetic stirrer and septum, and cooled to −15° C. Thereafter, 953.5 μl (10 mmol) of 2-bromopyridine are rapidly added dropwise. The solution immediately turns yellow. It is allowed to warm up to −10° C. The conversion of the reaction is determined as follows: about 100 μl solution are taken and introduced into 1 ml of a saturated ammonium chloride solution. If the solution "bubbles", not much Grignard has formed yet. The aqueous solution is extracted with a pipette of ether and the organic phase is dried over $Na_2SO_4$. A GC of the ethereal solution is recorded. When a large amount of pyridine has formed compared to 2-bromopyridine, conversions are high. At −10° C., there has been little conversion. After warming up to room temperature and stirring for 1-2 hours, the reaction solution turns brown-yellow. A GC test shows complete conversion. Now the Grignard solution can be slowly added dropwise with a syringe pump to a solution of 1.748 g (11 mmol) of dichloro-tert-butylphosphine in 10 ml of THF which has been cooled to −15° C. beforehand. It is important that the dichloro-tert-butylphosphine solution is cooled. At room temperature, considerable amounts of dipyridyl-tert-butylphosphine would be obtained. A clear yellow solution is initially formed, which then turns cloudy. The mixture is left to warm up to room temperature and to stir overnight. The solvent is removed under high vacuum and a whitish solid which is brown in places is obtained. The solid is suspended with 20 ml of heptane and the solid is comminuted in an ultrasound bath. After allowing the white solid to settle out, the solution is decanted. The operation is repeated twice with 10-20 ml each time of heptane. After concentration of the heptane solution under high vacuum, it is distilled under reduced pressure. At 4.6 mbar, oil bath 120° C. and distillation temperature 98° C., the product can be distilled. 1.08 g of a colourless oil are obtained. (50%).

Analytical data: $^1H$ NMR (300 MHz, $C_6D_6$): δ 8.36 (m, 1H, Py), 7.67 (m, 1H, Py), 7.03-6.93 (m, 1H, Py), 6.55-6.46 (m, 1H, Py), 1.07 (d, J=13.3 Hz, 9H, t-Bu)

$^{13}C$ NMR (75 MHz, $C_6D_6$): δ 162.9, 162.6, 148.8, 135.5, 125.8, 125.7, 122.8, 35.3, 34.8, 25.9 and 25.8.

$^{31}P$ NMR (121 MHz, $C_6D_6$) δ 97.9,

MS (EI) m:z (relative intensity) 201 ($M^+$, 2), 147(32), 145 (100), 109 (17), 78 (8), 57.1 (17).

Preparation of Compound 8

Preparation of 1,1-bis(tert-butyl-2-pyridylphosphino)ferrocene

Scheme 3: Synthesis of compound 8

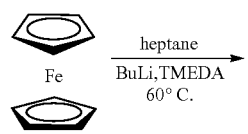

heptane
BuLi,TMEDA
60° C.

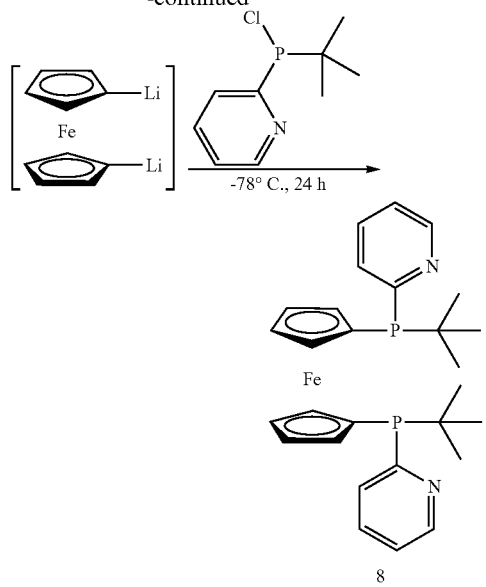

8

Variant A:

474.4 mg (2.55 mmol) of sublimed ferrocene are weighed out into a 50 ml round-bottom flask with magnetic stirrer and septum, and secured. Following addition of 15 ml of heptane, the ferrocene has completely dissolved. Then 841 μl of tetramethylethylenediamine (1.1 eq, 5.61 mmol) are added in one go and 2.04 ml of BuLi (2.5 M in hexane, 2.0 eq, 5.1 mmol) are added dropwise. After 2-3 hours an orange precipitate is formed. The mixture is stirred overnight, the heptane solution is decanted, and the orange solid is washed twice with heptane. Then a further 10 ml of heptane are added and the suspension is cooled to −70° C. 1.08 g (2.1 eq, 5.36 mmol) of chloro-2-pyridyl-tert-butylphosphine are dissolved in 7 ml of heptane. The solution is cloudy and must be filtered over Celite. A little insoluble white solid has formed. This solution is added dropwise to the dilithium ferrocene solution. In the course of warming to room temperature, the orange suspension lightens. In order to complete the reaction, the reaction solution is heated under reflux for about 1 hour. A clear orange solution and white precipitate have formed.

7 ml of argon-saturated water are added to the suspension. The white precipitate dissolves. Following removal of the aqueous phase, the procedure is repeated twice. In the course of these operations, the heptane phase becomes cloudy. Following complete removal of the organic phase under a high vacuum, an oily orange residue is left. This residue is taken up in 10 ml of ether and dried over $Na_2SO_4$ (crude yield 913 mg). At −28° C., overnight, neither a precipitate nor crystals are formed. Even a mixture of diethyl ether and heptane at −28° C. does not result in crystallization. A $^{31}P$ NMR of the solution again shows the product peak, now at 7.39 ppm, and a signal at 40.4 ppm. The product can be purified by column chromatography. The ether solution is applied under argon to a short column eluted with diethyl ether. The orange product front runs away right at the front and can easily be collected. Removal of the ether gives 241 mg (16%) of a viscous orange oil in a purity of approximately 95%.

Variant B:

Batch size: 650.17 mg (3.495 mol) of ferrocene (sublimed), 2.8 ml (2 eq, 6.99 mmol) of 2.5 M BuLi (n-butyllithium), 1.1 ml (2.1 eq, 7.3 mmol) of tetramethylethylenediamine and 1.48 g (2.1 eq, 7.34 mmol) of chloro-2-pyridyl-tert-butylphosphine.

The dilithium salt of the ferrocene is again prepared in 15 ml of heptane. The chloro-2-pyridyl-tert-butylphosphine is dissolved, instead of in heptane, in 10 ml of THF, since the chlorophosphine dissolves better in THF. The work-up procedure was likewise optimized: after the boiling under reflux, the reaction mixture is quenched with just 1 ml of $H_2O$ and the solvent (heptane and THF) is removed completely under a high vacuum. The dark-yellow-orange, tough solid is taken up in 8 ml of $H_2O$ and 15 ml of diethyl ether and stirred for 1 minute. Following phase separation, the aqueous phase is removed by syringe and the organic phase is washed three times with $H_2O$. The organic phase is dried over $Na_2SO_4$ and filtered. The product is washed out of the $Na_2SO_4$ with three times 10 ml of diethyl ether until the solution is virtually colourless. The dark-orange solution is concentrated to a volume of 10 ml and passed under argon through a column containing silica gel 60. The eluent used is again diethyl ether. The filtrate is substantially lighter and orange. Removal of the solvent gives 1.16 g of a tough orange solid (64%).

Preparation of Compound 4 (α,α'-bis(2-pyridyl(t-butyl)phosphino)o-xylene)

Scheme 4: Synthesis of compound 4
(according to *Graham Eastham et al.* US 6335471 B1)

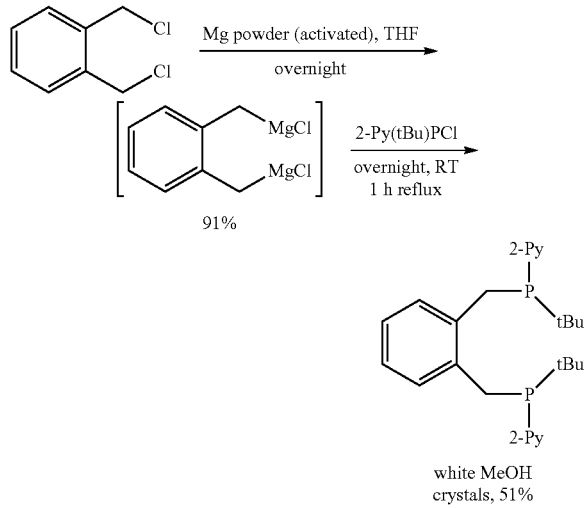

675 mg (27.8 mmol, 4 eq) of Mg powder are weighed out in a glovebox in a 250 ml round-bottom flask with a nitrogen tap and magnetic stirrer bar, and the flask is sealed with a septum. High vacuum is applied to the round-bottom flask (about $5\times10^{-2}$ mbar) and it is heated to 90° C. for 45 minutes. After cooling down to room temperature, 2 grains of iodine are added and the mixture is dissolved in 20 ml of THF. The suspension is stirred for about 10 minutes until the yellow colour of the iodine has disappeared. After the magnesium powder has settled out, the cloudy THF solution is decanted and the activated magnesium powder is washed twice with 1-2 ml of THF. Then another 20 ml of fresh THF are added. At room temperature, a solution of 1.21 g (6.9 mmol) of α,α'-dichloro-o-xylene in 70 ml of THF is slowly added dropwise with a syringe pump. The THF solution gradually turns a darker colour. The next day, the THF suspension is filtered to remove the unconverted magnesium powder and the content of Grignard compound is determined as follows:

1 ml of Grignard solution is quenched in a saturated aqueous solution of $NH_4Cl$ and extracted with ether, and dried with $Na_2SO_4$.

Quantitative Determination of the Content of the Grignard Solution:

1 ml of Grignard solution is quenched with 2 ml of 0.1 M HCl and the excess acid is titrated with 0.1 M NaOH. A suitable indicator is an aqueous 0.04% bromocresol solution. The colour change goes from yellow to blue. 0.74 ml of 0.1 M NaOH has been consumed. 2 ml-0.74 ml=1.26 ml, corresponding to 0.126 mmol of Grignard compound. Since a di-Grignard is present, the Grignard solution is 0.063 M. This is a yield exceeding 90%.

In a 250 ml three-neck flask with reflux condenser and magnetic stirrer, under argon, 1.8 g (8.66 mmol) of chlorophosphine (2-Py(tBu)PCl) are dissolved in 10 ml of THF and cooled to −60° C. Then 55 ml of the above-stipulated Grignard solution (0.063 M, 3.46 mmol) are slowly added dropwise at this temperature with a syringe pump. The solution at first remains clear and then turns intense yellow. After 1.5 hours, the solution turns cloudy. The mixture is left to warm up to room temperature overnight and a clear yellow solution is obtained. To complete the reaction, the mixture is heated under reflux for 1 hour. After cooling, 1 ml of $H_2O$ is added and the solution loses colour and turns milky white. After removing THF under high vacuum, a stringy, pale yellow solid is obtained. 10 ml of water and 10 ml of ether are added thereto, and two homogeneous clear phases are obtained, which have good separability. The aqueous phase is extracted twice with ether. After the organic phase has been dried with $Na_2SO_4$, the ether is removed under high vacuum and a stringy, almost colourless solid is obtained. The latter is dissolved in 5 ml of MeOH while heating on a water bath and filtered through Celite. At −28° C., 772 mg of product are obtained in the form of white crystals overnight. (51%). After concentration, it was possible to isolate another 100 mg from the mother solution. The overall yield is 57.6%, $^1$H NMR (300 MHz, $C_6D_6$): δ 8.58 (m, 2H, Py), 7.31-7.30 (m, 2H, benzene), 7.30-7.22 (m, 2H, Py), 6.85-6.77 (m, 2H, Py), 6.73 (m, 2H, benzene), 6.57-6.50 (m, 2H, py), 4.33 (dd, J=13.3 and 4.3 Hz, 2H, $CH_2$), 3.72-3.62 (m, 2H, $CH_2$), 121 (d, J=11.8 Hz, 18H, tBu).

$^{13}$C NMR (75 MHz, $C_6D_6$); δ 161.3, 161.1, 149.6, 137.8, 137.7, 134.5, 133.3, 132.7, 131.4, 131.3, 125.7, 122.9, 30.7, 30.5, 28.2, 28.0, 26.5, 26.4, 26.2, and 26.1.

$^{31}$P NMR (121 MHz, $C_6D_6$) δ 8.8.

EA calculated for $C_{26}H_{34}N_2P_2$: C, 71.54; H, 7.85; N, 6.56; P, 14.35. Found: C, 71.21; H, 7.55; N, 6.56; P, 14.35.

High-Pressure Experiments

Feedstocks:
Methanol (MeOH)
Ethene (Also Referred to as Ethylene

General Method for Performance of the High-Pressure Experiments

General Experiment Description for Reactions in Batchwise Mode:

Depending on the palladium precursor, 0.04 mol %, based on the ethylene, are weighed out under argon, and 0.16 mol % of the corresponding ligand are weighed out, into a 25 ml Parr reactor (Parr autoclave) which can be given gastight sealing. 5 ml of methanol are added. Then 1 g of ethylene (35.7 mmol) is transferred into the autoclave (monitored via weighing of the autoclave). The autoclave is heated to 80° C. The autogenous pressure of the ethylene at 80° C. is now 20 bar. 30 bar of CO are injected at this point. At this temperature, the autoclave is stirred for 20 h and the pressure drop is measured using a pressure sensor and the Specview software from Parr Instruments. The yields of product indicated in the diagram are in agreement with the consumption of gas. The autoclave is subsequently cooled to room temperature and the pressure is let off. The contents of the autoclave are transferred to a 50 ml Schlenk vessel, and 1 ml of isooctane is added as an internal standard. The yield of methyl propionate is determined by GC analysis.

Analysis:

GC analysis of the products from ethene: for the GC analysis, an Agilent 7890A gas chromatograph having a 30 m HP column is used. Temperature profile: 35° C., 10 min: 10° C./min to 200° C., 16.5 min; the injection volume is 1 µl with a split of 50:1. Retention time of methyl propionate: 6.158 min Methanol Analysis Methanol was pretreated in a solvent drying unit: Pure Solv MD-/Solvent purification system, Innovative Technology Inc. One Industrial Way, Amesbury Mass. 01013

Water Values:

Determined by Karl Fischer titration: TitraLab 580-TIM580, Radiometer Analytical SAS (Karl-Fischer Titration), water content: measurement ranges, 0.1-100% w/w, measured water content: 0.13889%

The following were used:

Technical methanol from Applichem: No. A2954,5000, batch number: LOT: 3L005446

Water content max. 1%

Methanol from Acros Organics (via molecular sieve): water content 0.005%, code number: 364390010, batch number: LOT 1370321

TON: turnover number, defined as moles of product per mole of catalyst metal

TOF: turnover frequency, defined as TON per unit time for the attainment of a particular conversion, e.g. 50%

The n/iso ratio indicates the ratio of olefins converted terminally esters to olefins converted internally to esters.

The n selectivities reported hereinafter relate to the proportion of terminal methoxycarbonylation based on the overall yield of methoxycarbonylation products.

Ethylene Example

Scheme 5: Methoxycarbonylation of ethene.

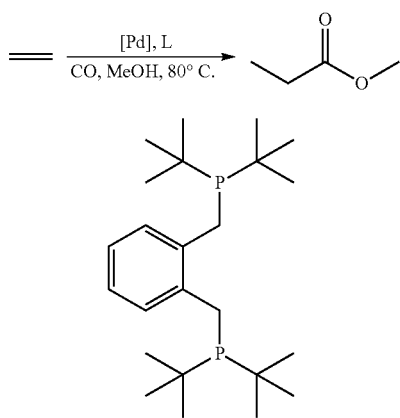

3

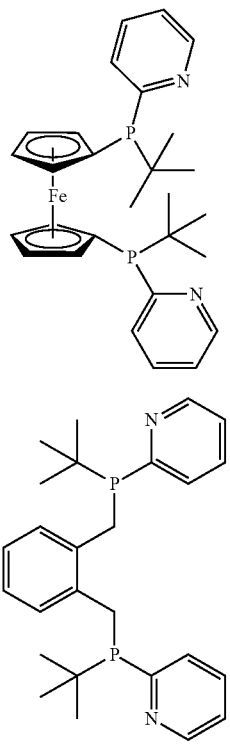

PdCl$_2$/3 (Comparative Example)

A 25 ml Parr autoclave is charged under argon with PdCl$_2$ (2.53 mg, 0.04 mol % based on the amount of substance of ethylene) and 3 (22.5 mg, 0.16 mol % based on the amount of substance of ethylene) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis is carried out for determination of yield. The yield is 20%.

PdCl$_2$/8

A 25 ml Parr autoclave is charged under argon with PdCl$_2$ (2.53 mg, 0.04 mol % based on the amount of substance of ethylene) and 8 (29.5 mg, 0.16 mol % based on the amount of substance of ethylene) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis is carried out for determination of yield. The yield is 100%.

PdCl₂/4

A 25 ml Parr autoclave is charged under argon with PdCl₂ (2.53 mg, 0.04 mol %, here and always hereinafter, based on the amount of substance of ethylene) and 4 (29.5 mg, 0.16 mol %, here and always hereinafter, based on the amount of substance of ethylene) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis is carried out for determination of yield. The yield is 100%.

Pd(acac)₂/3 (Comparative Example)

A 25 ml Parr autoclave is charged under argon with Pd(acac)₂ (4.34 mg, 0.04 mol %) and 3 (22.5 mg, 0.16 mol %) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. Yield of product is not detectable.

Pd(acac)₂/8

A 25 ml Parr autoclave is charged under argon with Pd(acac)₂ (4.34 mg, 0.04 mol %) and 8 (29.5 mg, 0.16 mol %) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 60%.

Pd(acac)₂/4

A 25 ml Parr autoclave is charged under argon with Pd(acac)₂ (4.34 mg, 0.04 mol %) and 4 (24.9 mg, 0.16 mol %) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 29%.

Pd(OAc)₂/8

A 25 ml Parr autoclave is charged under argon with Pd(OAc)₂ (3.2 mg, 0.04 mol %) and 8 (29.5 mg, 0.16 mol %) and 5 ml of methanol. Then 1 g (35.7 mmol) of ethylene is transferred into the autoclave. Mass is monitored via weighing of the autoclave. The autoclave is heated to 80° C. The pressure in the autoclave at this point is 20 bar at 80° C. Then 30 bar of CO are injected. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 58%.

The results are shown in FIG. 1

FIG. 1: Effect of the palladium precursor on the methoxycarbonylation of ethylene with ligands 3, 4 and 8.

As is clearly apparent, with the PdCl₂/ligand 8 combination without addition of an acid, a yield of >90% of methyl propionate is achieved after only around 2 hours, with a turnover frequency of 3700 mol of product/(mol Pd*h) based on a yield of 30%. Similarly good values are achieved with ligand 4. Here there is 90% yield after around 3 hours with a turnover frequency of 400. In comparison to this, the comparative ligand DTBPMB (3) shows a yield of around 20% with a turnover frequency of 27 only after 20 hours. Similarly, the use of Pd acetylacetonate or Pd acetate as a metal precursor in combination with the ligand for inventive use still leads to measurable yields in the acid-free system, whereas ligand 3 is no longer catalytically active.

FIG. 2: Acid-free methoxycarbonylation of ethene with ligands 3, 4 and 8

FIG. 2 shows results for the acid-free methoxycarbonylation of ethylene with ligands 3, 4 and 8. The reference point is the methoxycarbonylation with ligand 8 and the Pd compound palladium acetate Pd(OAc)₂ at 80° C. By raising the temperature to 120° C. it is possible to boost the yield of methyl propionate in 20 hours from 50% to 84%. With ligand 4 it is possible at 120° C. to achieve a yield of as much as 87% after 20 hours. The comparative ligand DTBPMB (3) gives a yield of only 3% in the acid-free system. The experiments are described in detail below.

Pd(OAc)₂/8

A 25 ml Parr autoclave is charged under argon with Pd(OAc)₂ (3.2 mg, 0.04 mol %) and 8 (29.5 mg, 0.16 mol %) and 5 ml of methanol. Then 1 g (35.7 mmol) of ethylene is transferred into the autoclave. Mass is monitored via weighing of the autoclave. Then 30 bar of CO are injected. The autoclave is heated to 80° C. The contents are stirred at 80° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 50%.

Pd(OAc)₂/8

A 25 ml Parr autoclave is charged under argon with Pd(OAc)₂ (3.2 mg, 0.04 mol %) and 8 (29.5 mg, 0.16 mol %) and 5 ml of methanol. Then 1 g (35.7 mmol) of ethylene is transferred into the autoclave. Mass is monitored via weighing of the autoclave. Then 30 bar of CO are injected. The autoclave is heated to 100° C. The contents are stirred at 100° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 64%.

Pd(OAc)₂/8

A 25 ml Parr autoclave is charged under argon with Pd(OAc)₂ (3.2 mg, 0.04 mol %) and 8 (29.5 mg, 0.16 mol %) and 5 ml of methanol. Then 1 g (35.7 mmol) of ethylene is transferred into the autoclave. Mass is monitored via weighing of the autoclave. Then 30 bar of CO are injected. The autoclave is heated to 120° C. The contents are stirred at 120° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 84%.

Pd(OAc)₂/3 (Comparative Example)

A 25 ml Parr autoclave is charged under argon with Pd(OAc)₂ (3.2 mg, 0.04 mol %) and 3 (22.5 mg, 0.16 mol %) and 5 ml of methanol. Then 1 g (35.7 mmol) of ethylene is transferred into the autoclave. Mass is monitored via weighing of the autoclave. Then 30 bar of CO are injected. The autoclave is heated to 120° C. The contents are stirred at 120° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 3%.

Pd(OAc)₂/4

A 25 ml Parr autoclave is charged under argon with Pd(OAc)₂ (3.2 mg, 0.04 mol %) and 4 (24.9 mg, 0.16 mol %) and 5 ml of methanol. Then 1 g (35.7 mmol) of ethylene is transferred into the autoclave. Mass is monitored via weighing of the autoclave. Then 30 bar of CO are injected. The autoclave is heated to 120° C. The contents are stirred at 120° C. for 20 h and the pressure drop in the autoclave is measured. The autoclave is then cooled and the residual pressure is let off. The contents of the autoclave are then transferred to a 50 ml Schlenk vessel and admixed with 1 ml of isooctane as an internal standard. A GC analysis takes place for determination of yield. The yield is 87%.

The invention claimed is:
1. An acid-free alkoxycarbonylation process comprising the following process steps:
 a) introducing an ethylenically unsaturated compound;
 b) adding a ligand-metal complex comprising Pd and a bidentate phosphine ligand, or adding a bidentate phosphine ligand and a compound which comprises Pd;
 c) adding an alcohol;
 d) supplying CO;
 e) heating the reaction mixture, the ethylenically unsaturated compound being reacted to form an ester in the presence of a Brønsted acid at low concentration,
 where the reaction mixture has less than 0.1 mol %, based on the amount of substance of the ethylenically unsaturated compound, of Brønsted acids having an acid strength of pKa≤3 or an acid strength of a pKa≤5, where the Brønsted acid results from the reaction course and
wherein the bidentate phosphine ligand is selected from a compound according to one of the formulae (I) and (II)

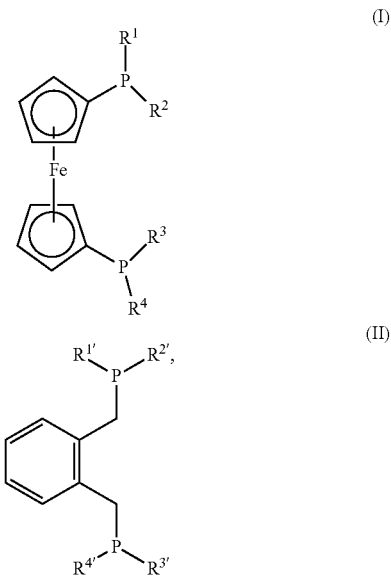

where
$R^1$, $R^2$, $R^3$, $R^4$, $R^{1'}$, $R^{2'}$, $R^{3'}$, $R^{4'}$ are each independently selected from —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl, —($C_3$-$C_{20}$)-heteroaryl;
at least one of the $R^1$, $R^2$, $R^3$, $R^4$ radicals or at least one of the $R^{1'}$, $R^{2'}$, $R^{3'}$, $R^{4'}$ radicals is a —($C_3$-$C_{20}$)-heteroaryl radical;
and
$R^1$, $R^2$, $R^3$, $R^4$, $R^{1'}$, $R^{2'}$, $R^{3'}$, $R^{4'}$, if they are —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl or —($C_3$-$C_{20}$)-heteroaryl,
may each independently be substituted by one or more substituents selected from —($C_1$-$C_{12}$)-alkyl, —($C_3$-$C_{12}$)-cycloalkyl, —($C_3$-$C_{12}$)-heterocycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —S—($C_1$-$C_{12}$)-alkyl, —S—($C_3$-$C_{12}$)-cycloalkyl, —COO—($C_1$-$C_{12}$)-alkyl, —COO—($C_3$-$C_{12}$)-cycloalkyl, —CONH—($C_1$-$C_{12}$)-alkyl, —CONH—($C_3$-$C_{12}$)-cycloalkyl, —CO—($C_1$-$C_{12}$)-alkyl, —CO—($C_3$-$C_{12}$)-cycloalkyl, —N—[($C_1$-$C_{12}$)-alkyl]₂, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl, —($C_3$-$C_{20}$)-heteroaryl-O—($C_1$-$C_{12}$)-alkyl, —COOH, —OH, —SO₃H, —NH₂ or halogen.

2. The process according to claim 1,
where $R^1$, $R^2$, $R^3$, $R^4$, $R^{1'}$, $R^{2'}$, $R^{3'}$ and $R^{4'}$, if they are —($C_1$-$C_{12}$)-alkyl, —($C_3$-$C_{12}$)-cycloalkyl, —($C_3$-$C_{12}$)-heterocycloalkyl, —($C_6$-$C_{20}$)-aryl or —($C_3$-$C_{20}$)-heteroaryl,
may each independently be substituted by one or more substituents selected from —($C_1$-$C_{12}$)-alkyl, —($C_3$-$C_{12}$)-cycloalkyl, —O—($C_1$-$C_{12}$)-alkyl, —O—($C_1$-$C_{12}$)-alkyl-($C_6$-$C_{20}$)-aryl, —O—($C_3$-$C_{12}$)-cycloalkyl, —($C_6$-$C_{20}$)-aryl, —($C_6$-$C_{20}$)-aryl-($C_1$-$C_{12}$)-alkyl, —($C_6$-$C_{20}$)-aryl-O—($C_1$-$C_{12}$)-alkyl, —($C_3$-$C_{20}$)-heteroaryl, —($C_3$-$C_{20}$)-heteroaryl-($C_1$-$C_{12}$)-alkyl or —($C_3$-$C_{20}$)-heteroaryl-O—($C_1$-$C_{12}$)-alkyl.

3. The process according to claim 1,
where at least two of the $R^1$, $R^2$, $R^3$, $R^4$ radicals or at least two of the $R^{1'}$, $R^{2'}$, $R^{3'}$, $R^{4'}$ radicals are a —($C_3$-$C_{20}$)-heteroaryl radical.

4. The process according to claim 3,
where the $R^1$ and $R^3$ radicals or the $R^{1'}$ and $R^{3'}$ radicals are each a —($C_3$-$C_{20}$)-heteroaryl radical.

5. The process according to claim 4,
where the $R^1$ and $R^3$ or $R^{1'}$ and $R^{3'}$ radicals are each a —($C_3$-$C_{20}$)-heteroaryl radical;
and the $R^2$ and $R^4$ or $R^{2'}$ or $R^{4'}$ radicals are each independently selected from —($C_1$-$C_{12}$)-alkyl, —($C_3$-$C_{12}$)-cycloalkyl, —($C_3$-$C_{12}$)-heterocycloalkyl or —($C_6$-$C_{20}$)-aryl.

6. The process according to claim 1,
where the radicals $R^1$, $R^2$, $R^3$ and $R^4$ and/or $R^{1'}$, $R^{2'}$, $R^{3'}$ and $R^{4'}$, if they are a heteroaryl radical, are a heteroaryl radical having five or six ring atoms.

7. The process according to claim 1,
where the radicals $R^1$, $R^2$, $R^3$ and $R^4$ and/or $R^{1'}$, $R^{2'}$, $R^{3'}$ and $R^{4'}$, if they are a heteroaryl radical, are selected from 2-furyl, 2-thienyl, N-methyl-2-pyrrolyl, N-phenyl-2-pyrrolyl, N-(2-methoxyphenyl)-2-pyrrolyl, 2-pyrrolyl, N-methyl-2-imidazolyl, 2-imidazolyl, 2-pyridyl or 2-pyrimidyl, the stated heteroaryl radicals not being further substituted.

8. The process according to claim 1,
where the bidentate phosphine ligand is selected from a compound according to one of the formulae (8) and (4)

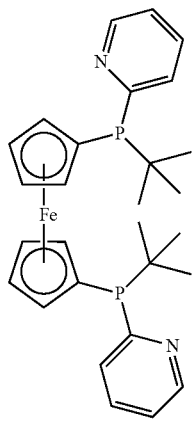

(8)

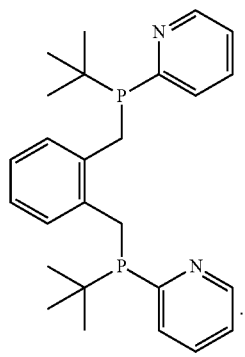

(4)

9. The process according to claim 1,
wherein the ethylenically unsaturated compound is selected from the group consisting of ethene, propene, 1-butene, cis- and/or trans-2-butene, isobutene, 1,3-butadiene, 1-pentene, cis- and/or trans-2-pentene, 2-methyl-1-butene, 3-methyl-1-butene, 2-methyl-2-butene, hexene, tetramethylethylene, heptene, 1-octene, 2-octene, di-n-butene, and mixtures thereof.

10. The process according to claim 1,
wherein the compound comprising Pd in process step b) is selected from palladium dichloride, palladium(II) acetylacetonate, palladium(II) acetate, dichloro(1,5-cyclooctadiene)palladium(II), bis(dibenzylideneacetone) palladium, bis(acetonitrile)dichloropalladium(II) or palladium(cinnamyl) dichloride.

11. The process according to claim 1,
wherein the alcohol in process step c) is selected from the group consisting of methanol, ethanol, 1-propanol, 1-butanol, 1-pentanol, 1-hexanol, 2-propanol, tert-butanol, 3-pentanol, cyclohexanol, phenol, and mixtures thereof.

12. The process according to claim 1,
where the reaction mixture is admixed with less than 0.1 mol %, based on the amount of substance of the ethylenically unsaturated compound, of Brønsted acids having an acid strength of $pKa \leq 5$.

* * * * *